United States Patent [19]

Huber-Enden

[11] 4,052,485

[45] Oct. 4, 1977

[54] PERFLUORO COMPOUNDS CONTAINING PHOSPHORUS

[75] Inventor: Helmut Huber-Emden, Basel, Switzerland

[73] Assignee: Ciba-Geigy Corporation, Ardsley, N.Y.

[21] Appl. No.: 227,661

[22] Filed: Feb. 18, 1972

[30] Foreign Application Priority Data

Feb. 25, 1971 Switzerland .......................... 2731/71
Dec. 29, 1971 Switzerland ........................ 19121/71

[51] Int. Cl.² ............................ C07F 9/14; C07F 9/42
[52] U.S. Cl. .................................... 260/928; 8/116 P; 106/15 FP; 260/543 P; 260/931; 260/955; 260/977; 427/394; 428/277

[58] Field of Search ............... 260/955, 928, 931, 977, 260/543 P

[56] References Cited

FOREIGN PATENT DOCUMENTS 1,122,404  8/1968  United Kingdom ................. 260/955

*Primary Examiner*—Richard L. Raymond
*Attorney, Agent, or Firm*—Karl F. Jorda; Edward McC. Roberts; Prabodh I. Almaula

[57] ABSTRACT

Perfluoro compounds containing dichloro phosphoryl and/or dichlorophosphoryl radicals are provided which are obtained by reacting perfluoroalkylalkenes with phosphorus trichloride in the presence of oxygen. The compounds are useful to obtain oleophobic finishes on various substrates, especially on fibrous materials.

2 Claims, No Drawings

PERFLUORO COMPOUNDS CONTAINING PHOSPHORUS

The subject of the present invention are perfluoro compounds containing phosphorus, which are obtained by reaction of perfluoroalkylalkene compounds with phosphorus trihalides in the presence of oxygen or oxygen-containing gases. The perfluoro compounds can contain perfluoroalkyl radicals with 1 to 22 carbon atoms. The perfluoroalkylalkene compounds used as starting products can be perfluoroalkylvinyl compounds which are unsubstituted or substituted at the vinyl group, such as, for example, 1-perfluoroalkyl-2,2-dialkylvinyl compounds, wherein the perfluoroalkyl radicals contain 4 to 14 carbon atoms and the alkyl radicals each contain 1 to 22 carbon atoms. The perfluoro compounds containing phosphorus contain up to about 8 phosphorus atoms in the form of phosphoryl and/or phosphonyl radicals. Possible phosphorus trihalides are, for example, phosphorus tribromide and phosphorus triiodide, but especially phosphorus trichloride. The reaction takes place with exclusion of water or moisture.

The new reaction products containing phosphorus preferably correspond to the formula

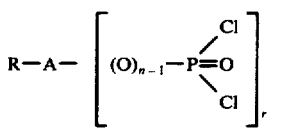

(1)

wherein R denotes a perfluoroalkyl radical with 1 to 22 carbon atoms, A denotes a radical of the formulae

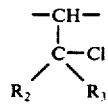

(2)

or

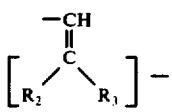

(3)

wherein the linkage with R is always via a methine group

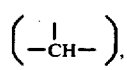, whilst the radical

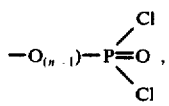, if $n = 2$, is also bonded via the methine group or, if $n = 1$ or 2, is bonded to the radicals $R_2$ and $R_3$, $R_2$ and $R_3$ each denote a hydrogen atom or an unbranched or branched hydrocarbon radical, preferably an alkyl radical with 1 to 22 carbon atoms, wherein the radical according to the formula (3) contains at least one alkyl group, and r denotes an integer having a value of 1 to 8, preferably of 1 to 4.

Compounds of the formula (1) in which r is 1 or 2 are particularly suitable. Further preferred compounds of the formula (1) are those which correspond to the formula

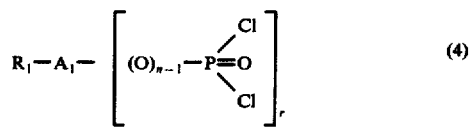

(4)

wherein $R_1$ denotes a perfluoroalkyl radical with 4 to 14 carbon atoms, $A_1$ denotes a radical of the formulae

(5)

or

(6)

wherein the linkage with R is always via a methine group

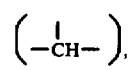, whilst the radical

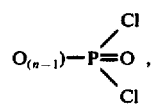, if $n = 2$, is also bonded via the methine group, or, if $n = 1$ or 2, is bonded to the radicals $R_2'$ and $R_3'$, $R_2'$ and $R_3'$ each denote a hydrogen atom or unbranched or branched alkyl radicals with 1 to 18 carbon atoms, with the radical according to the formula (6) containing at least one alkyl group, and r denotes an integer having a value of 1 to 8, preferably of 1 to 4.

The compounds mentioned, of the formula (1), can for example correspond to the formulae

(7)

wherein R denotes a perfluoroalkyl radical with 1 to 22 carbon atoms, Z denotes a radical of the formula

(7.1)

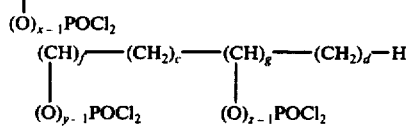

wherein $x$, $y$ and $z$ denote the figures 1 or 2, $e$, $f$ and $g$ denote the figures 0 or 1 and $a$, $b$, $c$ and $d$ denote integral numbers from 0 to 19, with the sum $(a + b + c + d + e + f + g)$ being at most 22, and B denotes a hydrogen atom or the radical Z, or to

(8)

wherein R, B and Z have the indicated meaning and at least one of the numbers $e$, $f$ and $g$ in the formula for Z is 1.

Compounds of the formulae (7) and (8) in which the radical R is a perfluoroalkyl radical with 4 to 14 carbon atoms, the sum $(a + b + c + d + e + f + g)$ is at most 12 and B represents a hydrogen atom, are preferred. As the number of the carbon atoms in the radical Z increases, compounds of the formula (3) are preferred.

The reaction products containing phosphorus correspond, for example, especially to the formula

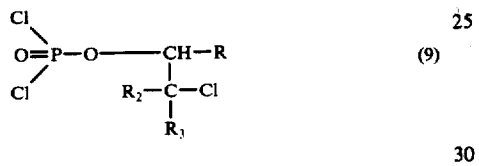
(9)

wherein R denotes a perfluoroalkyl radical with 1 to 22 carbon atoms and $R_2$ and $R_3$ each denote a hydrogen atom or an alkyl radical with 1 to 22 carbon atoms. If $n = 1$, the reaction products in question are perfluoroalkylalkylphosphonic acid dihalides, whilst for $n = 2$ the corresponding phosphoric acid compounds result. Both classes of compounds are produced alongside one another in the reaction according to the invention, but preferentially the phosphoric acid compounds. The reaction products preferably correspond to the formula

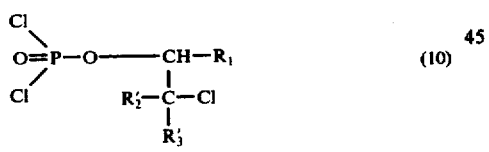
(10)

wherein $R_1$ denotes a perfluoroalkyl radical with 4 to 14 carbon atoms and $R_2'$ and $R_3'$ each denote a hydrogen atom or an alkyl radical with 1 to 18 carbon atoms. Further suitable compounds are the reaction products of the formula

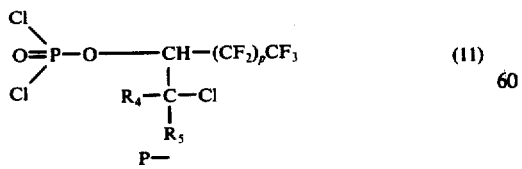
(11)

wherein $R_4$ and $R_5$ each denote a hydrogen atom or an alkyl radical with 1 to 12 carbon atoms and p denotes an integer having a value of 3 to 13.

The reaction products of the formula

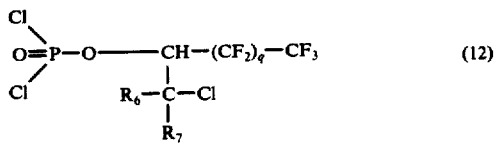
(12)

wherein $R_6$ and $R_7$ each denote a hydrogen atom or an alkyl radical with 1 to 8 carbon atoms and q denotes an integer having a value of 5 to 13, are particularly suitable.

The reaction products of the formula

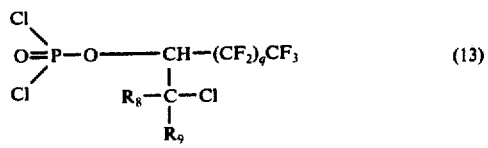
(13)

wherein $R_8$ and $R_9$ each denote a hydrogen atom or an alkyl radical with 1 to 4 carbon atoms and q has the indicated meaning, occupy a preferred position.

Amongst these, the compounds of the formulae

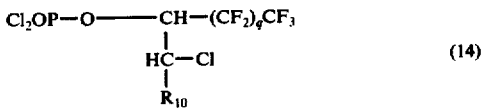
(14)

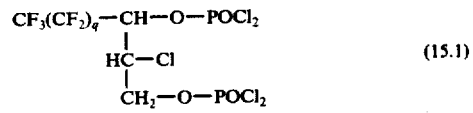
(15.1)

and

(15.2)

are particularly valuable. $R_{10}$ denotes a hydrogen atom or a methyl group and q has the indicated meaning.

The perfluoroalkyl radical of the perfluoroalkylalkyl compounds containing phosphorus preferably contains 4 to 14 carbon atoms. The perfluoroalkyl radical can be branched or unbranched. A branched radical can be, for example, an isoperfluoroalkyl radical of the formula

(16)

wherein $w$ represents an integer having a value of 1 to 11. Further, a so-called $\omega$-H-perfluoroalkyl radical which possesses a hydrogen atom in the terminal position, may be present. If $R_2$, $R_3$, $R_2'$, $R_3'$, $R_4$, $R_5$, $R_6$, $R_7$, $R_8$ or $R_9$ represent alkyl radicals, these may be branched or unbranched.

The perfluoroalkylalkyl compounds containing phosphorus are manufactured by reacting perfluoroalkylalkenes with phosphorus trihalides with exclusion of moisture and in the presence of oxygen or oxygen-containing gases.

The perfluoroalkylalkyl compounds containing phosphorus are also obtained if perfluoroalkylvinyl compounds of which the perfluoroalkyl radicals possess 1 to 22 carbon atoms and which are unsubstituted or substituted at the vinyl group are reacted with phosphorus trihalides in the presence of oxygen or oxygen-containing gases or if 1-perfluoroalkyl-2,2-dialkylethylenes wherein the perfluoroalkyl radical possesses 4 to 14 carbon atoms and the alkyl radicals each possess 1 to 22 carbon atoms, are reacted with phosphorus trihalides in the presence of oxygen or oxygen-containing gases.

Perfluoroalkylalkyl compounds containing phosphorus, of the formulae 1, 4 and 7 to 9 are obtained by reaction of perfluoroalkylalkenes of the formulae

or

wherein $R$, $R_1$, $R_2$ and $R_3$ have the indicated meaning, and phosphorus trichloride in the presence of oxygen or oxygen-containing gases.

The reaction products of the formulae (10) to (13) are manufactured analogously by reacting phosphorus trichloride with the perfluoroalkylalkenes of the formulae

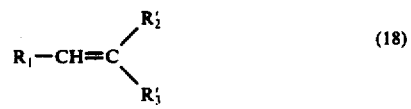

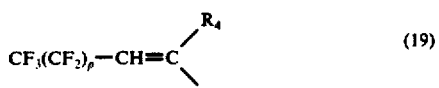

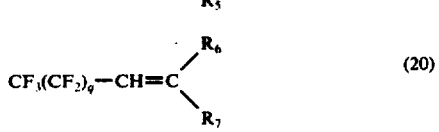

and

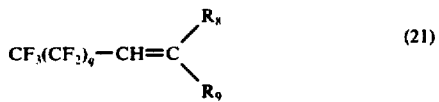

the reaction products of the formulae (14) and (15) are obtained from the compound of the formula

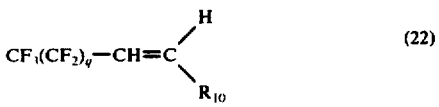

by reaction with phosphorus trichloride and oxygen. The substituents $R$, $R_1$, $R_2'$, $R_3'$, $R_4$, $R_5$, $R_6$, $R_7$, $R_8$, $R_9$ and $R_{10}$ as well as $p$ and $q$, in the formulae (18) to (22) have the indicated meaning.

When manufacturing the perfluoroalkylalkyl compounds containing phosphorus a possible procedure is to dissolve or suspend the perfluoroalkylalkene compound in an excess of the phosphorus trihalides and to pass a uniform, finely divided stream of air or oxygen through the reaction mixture whilst stirring well.

The reaction starts with an exothermic effect when oxygen or air is passed into the reaction mixture. If the reaction mixture is present as a suspension at the beginning of the reaction, it changes to a single phase during the reaction. After the exothermic reaction has finished, the reaction can be stopped. However, further phosphorus trihalide can also be added in order to react the perfluoroalkylalkene as completely as possible. The fine distribution of the gases is advantageously achieved by passing the gases through a porous plate or through using packings. The reaction can also advantageously be carried out in a closed apparatus under an oxygen atmosphere, only supplying as much oxygen as is consumed. A particularly appropriate method for the manufacture of the reaction products according to the invention is to add phosphorus trichloride in as small portions as possible, or slowly and continuously, to the initially introduced perfluoroalkylalkene compound in the presence of sufficient oxygen, waiting, in each case, for the resulting temperature rise in the reaction mixture to subside. Here again it is possible to pass the oxygen through the reaction mixture or to work under an oxygen atmosphere in a closed system. After completion of the addition of the phosphorus trichloride, the reaction is continued for some time whilst stirring. The reaction can furthermore be carried out in a solvent which is inert towards phosphorus trihalides and oxygen. Lower halogenated hydrocarbons, such as methylene chloride, chloroform and carbon tetrachloride, dichloroethane, 1,1,1-trichloroethane, trichloroethylene and esters of carboxylic acids, such as formic acid methyl ester and acetic acid methyl ester, as well as phosphorus oxychloride, are suitable for this purpose.

The molar ratio of the phosphorus halides to the perfluoro compounds is about 20:1 to 2:1, preferably 10:1 to 2:1.

The ratio of solvent to the phosphorus trihalides employed can vary within wide limits. Admittedly, it is desirable so to choose the ratio that there are 0.5 to 20 parts be weight of solvent, preferably 1 to 15 parts by weight, per 1 part by weight of the halide.

The reaction is carried out with exclusion of moisture. The temperature range in which the reaction can be carried out is approximately the range between the melting point and the boiling point of phosphorus trichloride, that is to say from $-91°$ C to $+75°$ C. However, the reactions are normally carried out at temperatures above $-70°$ C and a preferred range is that from $-5°$ C to $+25°$ C.

Depending on the nature of the reactants and on the choice of the reaction conditions, the reaction lasts about 1 to 12 hours; however, it is generally completed after 4 to 8 hours.

Working up is appropriately effected by distilling off the phosphorus oxyhalide produced during the reaction and subsequent vacuum distillation in order to purify the reaction products.

The reaction products are very reactive compounds since both the halogen atoms bonded to the phosphorus atom and the halogen atom in the $\beta$-position or $\gamma$-position to the phosphorus atom permit reactions with the most diverse reactants (substrates).

Because of their perfluoroalkyl part, the reaction products are suitable for the production of oleophobic finishes on porous and non-porous substrates, and can be incorporated into the material in question or, above all, be applied to its surface. The reactive halogen atoms in the reaction products can react with the substrates to form chemical bonds and can thus contribute to fixing the oleophobic agent onto the substrate. By porous substrates there are for example to be understood leather and paper, but preferably textile fibre materials, whilst possible non-porous materials are particularly metals and plastics, in addition to glass.

Textile fibre materials are of particular interest for finishing by means of the perfluoroalkyl compounds containing phosphorus. Such materials include, for example, those of natural or regenerated cellulose, such as cotton, linen or rayon, viscose or cellulose acetate, and also those of wool, synthetic polyamides, polyesters or acrylonitrile, as well as corresponding fibre mixtures. In these cases, the textiles can be in the form of filaments, fibres and flocks, but preferably of woven fabrics or knitted fabrics.

The reaction products are applied from organic solvent liquors in accordance with known processes, for example by the padding process or by the exhaustion process.

Suitable solvents for the application are, for example, solvents which are immiscible with water or of only restricted miscibility therewith, such as benzene and halogenated benzenes or benzenes substituted by low molecular alkyl groups, such as, for example, toluene, xylene, ethylbenzene, cumene, monochlorobenzene and dichlorobenzene; however, halogenated hydrocarbons are preferred, such as, for example, the solvents trichloroethylene and perchloroethylene used in the dry cleaning industry, and also chloroform, methylene chloride, carbon tetrachloride, dibromoethylene and the chlorinated ethanes, such as 1,1-dichloroethane, 1,2-dichloroethane, 1,1,1-trichloroethane and 1,1,2,2-tetrachloroethane. A further group are the water-miscible solvents such as, for example, ketones, such as acetone, methyl ethyl ketone and cyclohexanone; ethers and acetals, such as diisopropyl ether, diphenylene oxide, dioxane and tetrahydrofurane; additionally, pyridine, -acetonitrile, ethylene carbonate, γ-butyrolactone, N,N-dimethylformamide, N,N-dimethylacetamide, N-methylpyrrolidone, tetramethylurea, tetramethylenesulphone and others.

Mixtures of the solvents mentioned can also be used.

Preparations which contain the reaction products can contain further suitable additives, such as, for example, tertiary amines, which can improve the reaction between the finishing agent and the substrate. It is possible to use aliphatic and aromatic tertiary amines, such as, for example, trimethylamine, triethylamine or pyridine, which are employed in an amount of 1 to 5 mol, preferably 1 to 3 mol, relative to the amount of the reaction product to be applied. The temperature range for the application is as a rule between 20° and 110° C, preferably between 40° and 80° C. The treatment times for the application are as a rule between about 1 and 30 minutes, preferably 5 and 15 minutes. The treated material can be treated with organic solvents or water or aqueous sodium carbonate solution at room temperature or elevated temperature (40° to 100° C) without the oleophobic effect being lost. The finish is resistant to washing and to dry cleaning.

After the application and after treatment of the thus finished fabric with organic solvents, it is desirable to condition the fabric for some hours at room temperature. In the course thereof, it absorbs a natural moisture content, whereby the oleophobic effect of the finish is increased.

The amounts in which the reaction products are applied can vary within wide limits and are, for example, 0.1 to 10%, relative to the impregnating liquor, in the case of the padding process or, for example, 0.1 to 10%, preferably 0.5 to 5%, relative to the fibre material, if the exhaustion process is used.

The substrates treated in this way show a good oleophobic effect but at the same time also good wettability by water. Furthermore, so-called "soil release" and "antisoiling" effects can also be achieved with the perfluoro compounds containing phosphorus. The oleophobic agents can be applied in a separate process stage or together with the application of further finishing agents, provided these can be applied from organic solvents.

Because of their reactivity, the new fluorine compounds containing phosphorus are suitable for the manufacture of further valuable compounds which can be used as textile finishing agents.

In the examples which follow, unless otherwise stated, the parts denote parts by weight and the percentages denote percentages by weight.

Manufacturing Examples

EXAMPLE 1

48 g (0.11 mol) of a n-perfluoroalkylethylene homologue mixture of the formula $F(CH_2)_m—CH=CH_2$, which mainly contains the homologue with $m=8$, are introduced into 44.5 g (0.33 mol) of phosphorus trichloride. A 2-phase liquid mixture is produced. Oxygen is now passed in at 0° to +5° C whilst stirring well and excluding moisture, until the exothermic reaction ceases; in the course thereof, the mixture rapidly becomes a single-phase system. After 5 hours' reaction time, a further 44.5 g of phosphorus trichloride are added and oxygen is again passed in for 5 hours under the same conditions.

Thereafter, the phosphorus oxychloride produced is distilled off in a water pump vacuum; the residue is distilled in a high vacuum and 39.5 g (approx. 61% of theory) of the homologue mixture of the formula

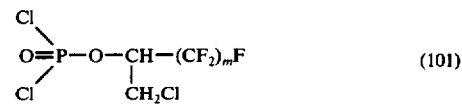 (101)

wherein $m$ is mainly 8, are obtained. The boiling point is 80° to 86° C at 0.005 mm Hg (Product A). The structure is confirmed by recording a mass spectrum, in that this shows a molecular weight of 614, which corresponds to the product of the formula

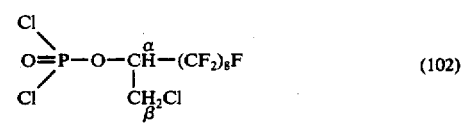 (102)

The nuclear resonance spectrum shows:
A multiplet at 5.2–6.0 ppm for $H_\alpha$ and
a doublet at 3.9 and 4.1 ppm for $H_\beta$.

EXAMPLE 2

98 g (0.21 mol) of a 1 n-perfluoroalkylpropene homologue mixture of the formula $F(CF_2)_m\text{—CH}=\text{CH—CH}_3$ with m having an approximate average value of 8 are mixed with 117 g (0.85 mol) of phosphorus trichloride, whereupon a homogeneous liquid mixture is produced.

Oxygen is passed in at 0° to +5° C, whilst stirring well and excluding moisture, until the exothermic reaction has ceased. After 2 hours, a further 117 g of phosphorus trichloride are added and oxygen is again passed in for 2 hours under the same conditions.

Thereafter, the resulting phosphorus oxychloride is distilled off in a water pump vacuum and the residue is distilled in a high vacuum. 88.4 g (68% of theory) of the homologue mixture of the formula

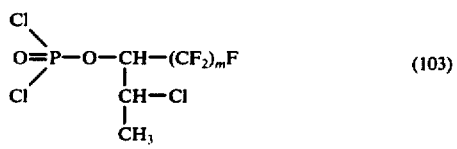 (103)

wherein m has an average value of 8, are obtained. The boiling point is 70° to 108° C at 0.005 mm Hg. The mixture partially crystallises on standing (Product B).

The structure is confirmed by recording a mass spectrum in that this shows a molecular weight of 628, which corresponds to the product of the formula

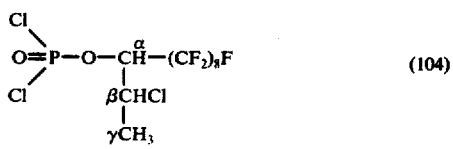 (104)

The nuclear resonance spectrum shows:
A multiplet at 4.75 - 6.5 ppm for $H_\alpha$
A multiplet at 3.9 - 4.7 ppm for $H_\beta$
A doublet at 1.6 and 1.75 ppm for $H_\gamma$.

EXAMPLE 3

The reactants according to Example 1 are reacted as follows: 44.6 g (0.1 mol) of n-perfluorooctylethylene (purity 95.8% as determined by gas chromatography) are reacted with 68.5 g (0.5 mol) of phosphorus trichloride under an oxygen atmosphere in a closed apparatus which is externally cooled with ice. The phosphorus trichloride is run in from a dropping funnel in about 50 portions, under the surface of the initially introduced perfluorooctylethylene, at 5° to 10° C. At the same time as much oxygen as is consumed is passed in. After each addition of phosphorus trichloride an exothermic reaction occurs, as a result of which the temperature of the reaction mixture transiently rises to 15°–30° C. After completion of the addition of phosphorus trichloride the reaction mixture is stirred for a further hour at 0° to 1° C. The duration of the total reaction is about 4 to 5 hours. Fractional distillation of the reaction mixture yields: 59.8 g (96.5% of theory) of phosphorus oxychloride (boiling point: 39°–40° C/70 mm Hg), and 55.2 g (93.7% of theory) of the compound of the formula

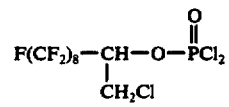

(Boiling point: 80°–81° C/0.002 mm Hg)

Analysis, calculated: C:19.5; H:0.5; Cl:17.3; P:5.0; found: C:19.6; H:0.5; Cl:17.2; P:5.1.

A repetition of the experiment with modified molar ratios (perfluorooctylethylene: phosphorus trichloride) gave the following results:

| | |
|---|---|
| Molar ratio 1:4 | Yield 89.4% |
| Molar ratio 1:3 | Yield 76.8% |

Further reactions with the same reactants are carried out as described. The factors changed are the number of portions of phosphorus trichloride which are added to the reaction mixture and the molar ratio of the reactants, and furthermore a solvent is in part used as the reaction medium.

0.1 mol of perfluorooctylethylene is reacted with X times 0.3 (X times 0.2) mol of phosphorus trichloride and with sufficient oxygen.

| X | Total amount of $PCl_3$ (mol) | Yield (%) | Recovered perfluorooctylethylene in % of the amount introduced. |
|---|---|---|---|
| 1 | 0.3 | 34.8 | 47.3 |
| 3 | 0.9 | 75.7 | 12.8 |
| 4 | 1.2 | 85.8 | 3.4 |
| 5 | 1.5 | 92.1 | 0.7 |
| 3 | 0.6 | 67.0 | 20.0 |
| 3 | 0.6 (Solvent $POCl_3$) | 62.6 | 21.8 |
| 3 | 0.6 (Solvent $CCl_4$) | 56.9 | 13.5 |

The following homologues of the compound described are also obtained analogously:

$F(CF_2)_6\text{—CH(CH}_2\text{Cl)—OPCl}_2\text{(=O)}$ — Boiling point: 78° C/0.005 mm Hg; Yield: 89.5%

$F(CF_2)_{10}\text{—CH(CH}_2\text{Cl)—OPCl}_2\text{(=O)}$ — Boiling point: 104° C/0.002 mm Hg; Melting point: 44–45° C; Yield: 90.4%

EXAMPLE 4

44.9 g (0.1 mol) of a homologue mixture $F(CF_2CF_2)_n\text{—CH}=CH_2$, which contains the following main components:

| n | 3 | 4 | 5 | 6 |
|---|---|---|---|---|
| mol % | 23.5 | 43.6 | 25.4 | 1.3 | are reacted in accordance with the process described in Example 3 with 82.3 g (0.6 mol) of phosphorus trichloride in the form of 50 identical portions, whilst passing in oxygen. Initially, the temperature rises exothermically to 5°–20° C, whilst towards the end of the reaction an exothermic rise to only 3°-7° C is observed. After 7 hours the addition of the phosphorus trichloride is complete and thereafter the reaction mixture is stirred for a further 3 hours at 0° to 2° C under an oxygen atmosphere. Practical distillation of the reaction mixture yields:

76.1 g (85.5% of theory) of POCl$_3$, boiling point 37°–42° C/70 mm Hg and 57.0 g (92.3% of theory) of a homologue mixture

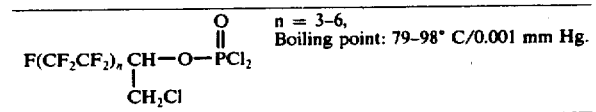

n = 3–6,
Boiling point: 79–98° C/0.001 mm Hg.

EXAMPLE 5

36 g (0.1 mol) of 1-n-perfluorohexylpropylene (1:5 cis-trans mixture) are reacted with 68.6 g (0.5 mol) of phosphorus trichloride in accordance with the process of Example 3. The reaction mixture is worked up by fractional distillation and the following reaction products are obtained:

1. 56 g of phosphorus oxychloride (boiling point 40°–42° C/70 mm Hg)

2. 39.8 g (75.2% of theory) of the product of the formula

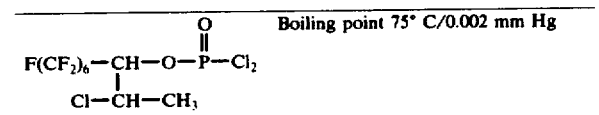

Boiling point 75° C/0.002 mm Hg

Analysis: calculated: C:20.4; H:0.9; Cl:20.1; P:5.9; found: C:20.6; H:1.2; Cl:18.6; P:6.1.

3. 8.2 g (13.2% of theory) of the product of the formula

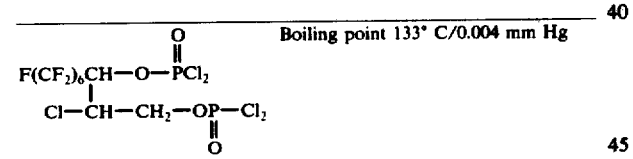

Boiling point 133° C/0.004 mm Hg

Analysis: calculated: C:16.3; H:0.6; Cl:26.8; P:9.3; found: C:16.7; H:0.7; Cl:25.2; P:9.3;

If 1-n-perfluorooctylpropylene is employed in the reaction, the following reaction products are obtained.

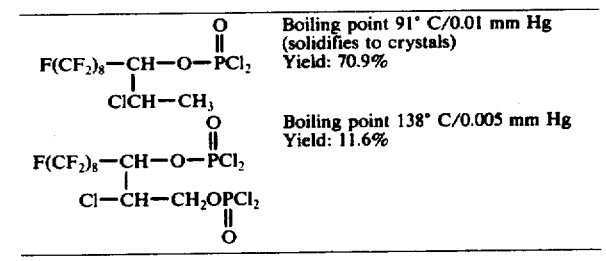

Boiling point 91° C/0.01 mm Hg (solidifies to crystals) Yield: 70.9%

Boiling point 138° C/0.005 mm Hg Yield: 11.6%

EXAMPLE 6

42.4 g (0.075 mol) of a perfluoroheptylbutene isomer mixture which is obtained by addition of perfluoroheptyl iodide to isobutylene and alkaline elimination of hydrogen iodide, are reacted in accordance with the process described in Example 3 with 44.9 g (0.33 mol) of phosphorus trichloride and oxygen. Duration of the reaction, 3 hours. Thereafter the reaction mixture is stirred for a further hour at 0° to 2° C whilst simultaneously passing in oxygen.

Fractional distillation of the reaction mixture results in the recovery of 15.3 g of the unreacted starting product. Additionally, the following are obtained:

I. 7.3 g of an oily mixture of boiling range 34°–90° C/0.02 mm Hg

II. 10.85 g of an oily mixture of boiling range 90°–101° C/0.02 mm Hg

III. 8.6 g of distillation residue.

Fractions I and II are again distilled and yield:

a. 3.4 g of an isomer mixture of boiling point 30° C/0.005 mm Hg. A calculated overall formula C$_{11}$H$_7$Cl$_3$F$_{15}$O$_2$P gives the following analytical data:

Calculated: C:22.3; H:1.2; Cl:17.9; P:5.2; Found: C:21.5; H:1.2; Cl:17.5; P:5.1.

This indicates the following structural formula:

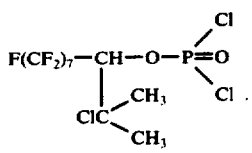

b. 7.6 g of an isomer mixture of boiling point 87° C/0.003 mm Hg

A calculated overall formula C$_{11}$H$_6$Cl$_2$F$_{15}$O$_2$P gives the following analytical data:

Calculated: C:23.7; H:1.1; Cl:12.7; P:5.6; Found: C:23.7; H:1.4; Cl:13.2; P:6.1.

This indicates the following structural formula:

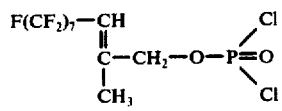

EXAMPLE 7

48 g (0.1 mol) of a perfluoroheptyloctene isomer mixture which is obtained by addition of n-perfluoroheptyl iodide to n-octene-(1) and subsequent alkaline elimination of hydrogen iodide are reacted, in accordance with the process described in Example 6, with 82.4 g (0.6 mol) of PCl$_3$ in the form of 20 equal portions, in the presence of oxygen. After addition of each portion of phosphorus trichloride, the temperature of the reaction mixture rises to 15°–20° C. The reaction lasts about 6 to 7 hours and thereafter oxygen is passed through the reaction mixture for about a further hour at 0°–1° C.

Fractional distillation yields:

1. 55.1 g of phosphorus oxychloride, boiling point: 39°–41° C/70 mm Hg 2. 7.1 g of unreacted starting material, boiling point: 55°–85° C/0.5 mm Hg 3. 53.4 g of reaction product mixture which cannot be distilled without decomposition.

Fraction 2 is shaken with dilute sodium hydroxide solution in order to remove acid impurities. 5.65 g (11.8%) of starting material are recovered as an oily phase.

50 g of Fraction 3 are added to 200 g of absolute methanol whilst stirring. Thereafter the reaction vessel is left for one hour at room temperature and the excess methanol is then distilled off. The residue is dissolved in 200 ml of chloroform and is then treated with saturated aqueous sodium bicarbonate solution until the aqueous phase reacts alkaline. The organic phase is separated off, dried over sodium sulphate and then freed of the solvent. 32 g of an oily residue are obtained.

The residue is fractionally distilled and 25.1 g of distillate and 3.7 g of residue are obtained within the range of 80° C/0.03 mm Hg to 176° C/0.05 mm Hg. The further fractionation yields the following reaction products:

Group 1 — boiling point: 135°–141° C/0.05 mm Hg, 13 g

Group 2 — boiling point: 171°–176° C/0.05 mm Hg, 3.5 g

Group 1 essentially contains an isomer mixture ($M_1$ and $M_2$) of probable formula $$F(CF_2)_7-CH=CH-(CH_2)_k-\underset{\underset{n=1\ or\ 2}{(O)_{n-1}-PO(OCH_3)_2}}{CH}-(CH_2)_l-H \quad k+l=5$$

Analysis: Calculated: $M_1(n=1)$; C:34.7; H:3.4; P:5.3; M = 588; $M_2(n=2)$; C:33.8; H:3.3; P:5.1; M = 604; Found: C:33.9; H:3.6; P:5.8; M = 577.

Mass spectrum: $M_1$ = 588; found: 589 = $M_1$ + H; 587 = $M_1$ − H. $M_2$ = 604; found: 605 = $M_2$ + H; 603 = $M_2$ − H.

Group 2 contains isomer mixtures ($M_3$-$M_6$) of the probable formulae $$F(CH_2)_7\underset{\underset{O}{\underset{\|}{O-P-(OCH_3)_2}}}{\overset{Cl}{CH}}-CH-(CH_2)_k-\overset{(O)_{n-1}\overset{O}{\overset{\|}{P}}-(OCH_3)_2}{CH}-(CH_2)_l-H$$

and $$F(CH_2)_7-CH=CH-(CH_2)_k-\overset{(O)_{n-1}\overset{O}{\overset{\|}{P}}(OCH_3)_2}{CH}-(CH_2)_l-\overset{(O)_{o-1}\overset{O}{\overset{\|}{P}}-(OCH_3)_2}{CH}-(CH_2)_m-H$$

$M_3$ n = 1
$M_4$ n = 2
k + l = 5

$M_5$ n = 1 o = 2 or n = 2 o = 1
$M_6$ n = 2 o = 2
k + l + m = 4

Analysis: calculated: $M_3$; C:30.5; H:3.5; Cl:4.7; P:8.3; M = 749; $M_4$; C:29.8; H:3.4; Cl:4.6; P:8.1; M = 765; $M_5$; C:32.0; H:3.5; P:8.7; M = 712; $M_6$ C:31.3; H:3.5; P:8.5; M = 728; found: C:31.7; H:3.5; Cl:1.4; P:8.1; M = 704.

Mass spectra: $M_3$ = 748 (Cl-35); found: 749 = $M_3$ + H; 747 = $M_3$ − H. $M_4$ = 764 (Cl-35); found: 765 = $M_4$ + H; 763 = $M_4$ − H. $M_5$ = 712; found: 713 = $M_5$ + H; 711 = $M_5$ − H. $M_6$ = 728; found: 729 = $M_6$ + H; 727 = $M_6$ − H.

EXAMPLES OF USES

EXAMPLE 8 a. A cotton or woollen fabric is impregnated with a 5% strength solution of the reaction products according to Examples 1 and 2 (A,B) in dry benzene, lightly squeezed out and then heated to 100° C for 30 minutes in a drying cabinet. The samples thus treated are tested for their oil repellency. The oil-repellent effect is assessed in accordance with the so-called "3 M oil repellency test" (Crajeck and Petersen, Textile Research Journal 32, 320 to 331, 1960) using heptane-Nujol mixtures. In the assessment, 150 denotes the best achievable rating.

b. The samples treated in this way are washed in carbon tetrachloride at room temperature, and dried.

c. The samples treated in this way are washed for 10 minutes in water, the cotton fabric at 100° C and the woollen fabric at 40° C. They are then dried in a stream of hot air.

d. The samples treated in this way are washed for 10 minutes in 5% strength sodium carbonate solution, the cotton fabric at 100° C and the woollen fabric at 40° C. Thereafter the fabrics are well rinsed with water and dried in a stream of hot air. The results of the test are summarised in the table below:

|           | Substrate |     |      |     |
|-----------|-----------|-----|------|-----|
|           | Cotton    |     | WOol |     |
| Treatment | A         | B   | A    | B   |
| a         | 150       | 140 | 120  | 140 |
| b         | 150       | 140 | 120  | 140 |
| c         | 130       | 140 | 120  | 120 |
| d         | —         | 140 | 120  | 100 |

The fabrics which have been finished with the reaction product according to Examples 1 and 2 are oleophobic and hydrophilic.

EXAMPLE 9

The procedure of Example 8 is followed and the reaction products according to Examples 1 and 2 are applied, but from dry chloroform and in the presence of 0.34 g of triethylamine per g of reaction product.

The results are summarised in the table below:

|           | Substrate |     |      |     |
|-----------|-----------|-----|------|-----|
|           | Cotton    |     | Wool |     |
| Treatment | A         | B   | A    | B   |
| a         | 130       | 120 | 120  | 50  |
| b         | 130       | 120 | 50   | 50  |
| c         | 140       | 140 | 140  | 130 |

| | Substrate | | | |
|---|---|---|---|---|
| | Cotton | | Wool | |
| Treatment | A | B | A | B |
| d | 140 | 130 | 140 | 120 |

The fabrics which have been finished with the products according to Examples 1 and 2 (A,B) are oleophobic and hydrophilic.

I claim:

1. Perfluoro compounds containing phosphorus, of the formula

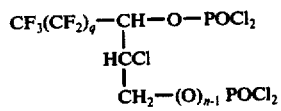

wherein $q$ denotes an integer having a value of 5 to 13 and $n$ is 1 or 2.

2. Perfluoro compounds containing phosphorus, of the formula

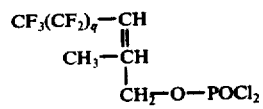

wherein $q$ is an integer having a value of 5 to 13.

* * * * *